United States Patent [19]

Heitmann

[11] 4,217,282
[45] Aug. 12, 1980

[54] PROCESS FOR MAKING N-(2-METHYL-1-NAPHTHYL)-MALEIMIDE

[75] Inventor: Wayne R. Heitmann, Gurnee, Ill.

[73] Assignee: Abbott Laboratories, North Chicago, Ill.

[21] Appl. No.: 13,099

[22] Filed: Feb. 21, 1979

[51] Int. Cl.$^2$ .................. C07D 207/44; C07D 207/40
[52] U.S. Cl. ..................... 260/326.5C; 260/326.5 FM
[58] Field of Search ............... 260/326.5 FM, 326.5 C

[56] References Cited

U.S. PATENT DOCUMENTS 4,141,905  2/1979  Becker et al. ............. 260/326.5 FM

*Primary Examiner*—Jose Tovar
*Attorney, Agent, or Firm*—Paul D. Burgauer; Robert L. Niblack

[57] ABSTRACT

A practical method for making N-(2-methyl-1-naphthyl)-maleimide has been discovered; it requires the use of specific solvents and acid catalysts which produce the desired compound in good yield and highly acceptable purity.

7 Claims, No Drawings

PROCESS FOR MAKING N-(2-METHYL-1-NAPHTHYL)-MALEIMIDE

DETAILED DESCRIPTION OF THE INVENTION

N-(2-methyl-1-naphthyl)-maleimide, hereinafter referred to simply as MNM, has recently been recognized as having unusual biocidal properties as more clearly demonstrated in U.S. Ser. No. 843,610 now U.S. Pat. No. 4,141,905, issued Feb. 27, 1979. While the previously described process for making MNM may be satisfactory for small quantities, a yield of 60% of theory for a commercially used product is not satisfactory.

It has now been found that MNM can be prepared in yields of 80% or above by the process consisting essentially in heating 2-methyl-1-naphthylamine and maleic anhydride in a molar ratio between 1:1 and 1:1.2 in the presence of an inert organic solvent which has a boiling point of 80° C. or above and a catalytic amount of an acid of the formula R—OP(OH)$_2$O or R'—OSO$_2$OH wherein R is H or loweralkyl and R' is loweralkyl, R-phenyl or R-benzyl, said heating being carried out at or above the temperature where water evaporates from the liquid mixture and being continued until the distillate is essentially free of water. The term "loweralkyl" is intended to represent a chain of 1-4 carbons.

MNM can be removed from the reaction mixture in various ways easily recognized by those skilled in the art. For instance, the reaction mixture can be concentrated, followed by fractional crystallization of the MNM from the concentrate; the above-named acid as well as any maleic acid can be neutralized with an acid acceptor, such as a trialkylamine, e.g., triethylamine, or an inorganic acid acceptor, such as calcium carbonate, sodium bicarbonate or the like or, depending on the solvent used, the desired MNM can be salted out.

The inert organic solvent referred to above is preferably one which boils within a range of 80° to 150° C. Excellent results are obtained by using dimethylformamide, commercial mixture of saturated hydrocarbons boiling within the above range, benzene, toluene, xylene or the like. As acid catalysts, phosphoric acid and alkylsulfonic acid are particularly suitable. These acids may be used in analytically pure or technical form, and are used in quantities corresponding to 0.2–2.0 molar percent, preferably about 0.5–1.0 molar percent, of the amount of 2-methyl-1-naphthylamine present in the condensation reaction.

Since one of the preferred solvents for the new process is toluene, the new process is particularly suited to prepare MNM from the reaction mixture that is obtained by catalytically hydrogenating 1-nitro-2-methylnaphthalene, the starting material used for making said 2-methyl-1-naphthylamine. The mentioned reaction mixture from said hydrogenation process only requires the removal of the catalyst since said hydrogenation is preferably carried out with toluene as the reaction medium.

When in the above reaction the acid catalyst is used in amounts above 1.0 molar percent, no adverse results are observed in the reaction, but removal of the excess or its neutralization may prove cumbersome or costly, without providing a substantial increase in reaction speed.

The reaction between maleic anhydride and 2-methyl-1-naphthylamine in the presence of the specified acid catalyst is almost instantaneous but, to insure that said reaction proceeds to MNM and not only to the monoester of maleic acid, heating of the reaction mixture for at least one hour is preferred. As specified, this heating is done at a temperature whereby the formed water evaporates. To assure substantial completion of the reaction, the heating step is carried out in such a fashion that the evaporating water is elminated from the reaction mixture. Completion of the reaction can easily be checked by analyzing successive portions of the distillate for absence of substantial amounts of water. Alternately, if all the materials used in the reaction are free of water or the amount of water therein is known, the reaction may be continued until the calculated reaction-formed water has distilled. In a practical sense, the reaction may be carried out for 3 hours at a temperature between the boiling point of the reaction mixture and 125° C. which assures essential completion of the reaction. Temperatures above 125° C. or heating beyond 3 hours ordinarily produce no increase in yield except where the used acid catalyst is deficient in purity or quantity.

To illustrate the process of the current invention, reference is made to the following examples which, however, are not intended to limit the invention in any respect:

EXAMPLES

Over a period of 30 minutes, 1.59 moles of 2-methyl-1-naphthylamine is added to a mixture of 1.91 moles of maleic anhydride and 0.079 moles of 98% pure methane sulfonic acid in 250 ml. of toluene. The reaction is heated to reflux during the addition of the amine and continued for about 2 hours thereafter. During this period, water is eliminated from the reflux stream. When the stream is essentially free of water, the mixture is cooled to 70°–80° C. and 0.11 moles of triethylamine is added to neutralize the methane sulfonic acid.

The desired MNM is isolated by adding 250 ml. of ethanol, cooling the slurry to 0°–5° C. and filtering. The product is washed with ethanol and dried at 50° C. in a vacuum oven, producing 1.36 moles (85.2% of theory) of MNM of 98.1% purity (shown by high pressure liquid chromatography).

When the above method is carried out with 70% pure (technical grade) methane sulfonic acid or an equimolar amount of phosphoric acid, yields of 84% and 73%, respectively, are obtained. Similar results are obtained by using 0.5 molar percentages of methane phosphoric acid, toluene sulfonic acid or benzene sulfonic acid.

However, when sulfuric acid, trichloroacetic acid, hydrochloric acid or similarly strong acids are used as the catalyst, the resulting reaction mixture is or contains a large amount of tar, making isolation of any useful product economically or technically infeasible.

I claim:

1. The process of making N-(2-methyl-1-naphthyl)-maleimide consisting essentially in heating 2-methyl-1-napthylamine and maleic anhydride in a molar ratio between 1:1 and 1:1.2 in the presence of an inert organic solvent which has a boiling point of 80° C. or above and a catalytic amount of an acid of the formula R—OP(OH)$_2$O or R'—OSO$_2$OH wherein R is H or loweralkyl and R' is loweralkyl, R-phenyl or R-benzyl, said heating being carried out at or above the temperature where water evaporates from the liquid mixture and being continued until the distillate is essentially free of water.

2. The process of claim 1 wherein said acid is methanesulfonic acid.

3. The process of claim 1 wherein said organic acid is used in an amount of at least 0.5 molar percent of said 2-methyl-1-naphthylamine.

4. The process of claim 1 wherein said organic solvent is toluene.

5. The process of claim 4 wherein said acid is methanesulfonic acid.

6. The process of claim 4 wherein said toluene and said 2-methyl-1-naphthylamine together are the crude reaction mixture obtained from the catalyst hydrogenation of 1-nitro-2-methylnaphthalene after removal of the catalyst.

7. The process of claim 1 wherein said organic solvent is benzene.

* * * * *